United States Patent
Su et al.

(10) Patent No.: US 7,377,183 B2
(45) Date of Patent: May 27, 2008

(54) FLOW MEASURING DEVICE AND MANUFACTURE METHOD THEREOF

(75) Inventors: Chun-min Su, Hsinchu (TW); Han-sheng Chuang, Hsinchu (TW); Yi-Lin Ho, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 11/525,577

(22) Filed: Sep. 22, 2006

(65) Prior Publication Data
US 2007/0119261 A1    May 31, 2007

(30) Foreign Application Priority Data
Nov. 29, 2005   (TW)   .............................. 94141971 A

(51) Int. Cl.
*G01F 1/58*       (2006.01)
(52) U.S. Cl. .................................................. 73/861.15
(58) Field of Classification Search ............. 73/861.04, 73/861.95, 196, 204.26, 204.25, 204.24
See application file for complete search history.

(56) References Cited

U.S. PATENT DOCUMENTS

| | | | | |
|---|---|---|---|---|
| 4,542,650 A | * | 9/1985 | Renken et al. ................. | 73/196 |
| 4,836,014 A | * | 6/1989 | Hilliard ......................... | 73/76 |
| 5,533,412 A | * | 7/1996 | Jerman et al. ........... | 73/861.95 |
| 5,597,961 A | * | 1/1997 | Marrelli ................... | 73/861.04 |

* cited by examiner

*Primary Examiner*—Jewel Thompson
(74) *Attorney, Agent, or Firm*—Silicon Valley Patent Group LLP

(57) ABSTRACT

A device for measuring a flow of a fluid is provided. The device includes a base, a channel, and at least two electronic circuits. The channel is mounted on the base, flowing the fluid therein and having at least two sections, and the at least two electronic circuits are electrically connected to the respective at least two sections, detecting a respective variation signal corresponding to the respective at least two sections so as to obtain the flow according to the respective variation signal.

26 Claims, 5 Drawing Sheets

(a)

(b)

FLOW MEASURING DEVICE AND MANUFACTURE METHOD THEREOF

FIELD OF THE INVENTION

The present invention relates to a flow measuring device and manufacture method thereof, in particular, to the structure of a flow measuring device and manufacture method thereof.

BACKGROUND OF THE INVENTION

Because of the progressiveness of micro-electromechanical techniques, the demands for miniature flow meter are increased day by day over the market, for example, to control a reagent at the aspect of biotechnology-medical or to be a blood-injecting pump meter etc. However, with the current techniques, the commercial miniature flow meter seldom provides a sufficient calibration method in accordance with the international standard for the flow measuring capability thereof. Hence the users cannot insure the reliability of measured data by the miniature flow meter.

Currently, only a few feasible miniature flow meters are available on the market. The metering principles thereof are categorized into two classifications as follows: thermal sensing type and pressure gradient type. The Sensirion SLG1430-025 developed by the Swiss trade, and the Thermal Flow Sensor developed by Dr. Tai, CIT are the well-known representatives of thermal sensing type miniature flow meter. The metering capabilities of both types are declared in the range from 50 nL/min to 1500 nL/min, but the maximum error of thermal sensing type miniature flow meter is up to 10%. The Miniature Flow Sensor developed by U.S. trade Seyonic is the well-known representative of pressure gradient type miniature flow meter. The minimum metering capability of pressure gradient type miniature flow meter approximates to around 300 μL/min. Nevertheless, up to the present, the aforementioned pressure gradient type miniature flow meter is still in the stage of experimental product.

With respect to the aspect of calibration method, it is not provided by the majority of the miniature flow meter products. The minority suchlike Dr. Tai, CIT provides some reference material explaining that the calibration method they adopted is by the following: a graduated syringe is connected to the end of the miniature flow meter, whereby a reading is readout for judging the accuracy of the instant flow rate. Because the aforementioned metering method bears errors due to the subjective presumption thereof, this calibrating method is generally considered insufficient.

In the case of Taiwan, Center for Measurement Standards, Industrial Technology Research Institute is one of the research institutes devoted to the field of micro flow measuring technique thereof, which center has devoted to develop the micro flow measuring standards since three years ago. Up to the present, the prototype technique using gravimetric method has been developed. However, since the gravimetric method is restricted by many external surroundings (such as the evaporation, the variation of the temperature/humidity etc.), the minimum measurable flow thereof barely comes to the level about 1 μL/min. Moreover, the micro flow measuring system configured with the gravimetric method is bulky and requires a highly stable condition for the external surroundings. Hence the system thereof is not feasible for the ordinary commercial usage, and is obviously not convenient enough.

To overcome the aforementioned drawbacks of the prior art, a novel device for measuring flow and the method manufacturing the novel device thereof is provided.

SUMMARY OF THE INVENTION

According to the aforementioned present invention, a device for measuring a flow of a fluid is provided. The device includes a base, a channel, and at least two electronic circuits. Wherein the channel is mounted on the base, flowing the fluid therein and having at least two sections, and the at least two electronic circuits are electrically connected to the respective at least two sections, detecting a respective variation signal corresponding to the respective at least two sections so as to obtain the flow according to the respective variation signal.

According to the aforementioned present invention, a device for measuring a flow of a fluid is provided. The device includes a plurality of bases, a plurality of channels, and at least two electronic circuits. The plurality of channels are mounted on the respective plurality of bases, flowing the fluid therein, wherein each of the plurality of channels has at least two sections, and the at least two electronic circuits are electrically connected to the respective at least two sections, detecting a respective variation signal corresponding to the respective at least two sections so as to obtain the flow according to the respective variation signal.

According to the aforementioned present invention, a method for fabricating a flow-measuring device is provided. The device includes a processor, and at least two electronic circuits. Wherein the at least two electronic circuits are electrically connected to the processor and respectively detecting a variation signal so as to obtain a flow rate of the micro fluid according to the variation signal.

According to the aforementioned present invention, a method for fabricating a flow-measuring device is provided. The method includes steps of (a) providing a base; (b) forming at least two pair of electrodes on said base; and (c) forming a channel on said base.

The foregoing and other features and advantages of the present invention will be more clearly understood through the following descriptions with reference to the drawings:

DETAILED DESCRIPTION OF THE PREFERRED EMBODIMENT

The present invention will now be described more specifically with reference to the following embodiments. It is to be noted that the following descriptions of preferred embodiments of this invention are presented herein for the aspect of illustration and description only; it is not intended to be exhaustive or to be limited to the precise form disclosed.

Figure 1:
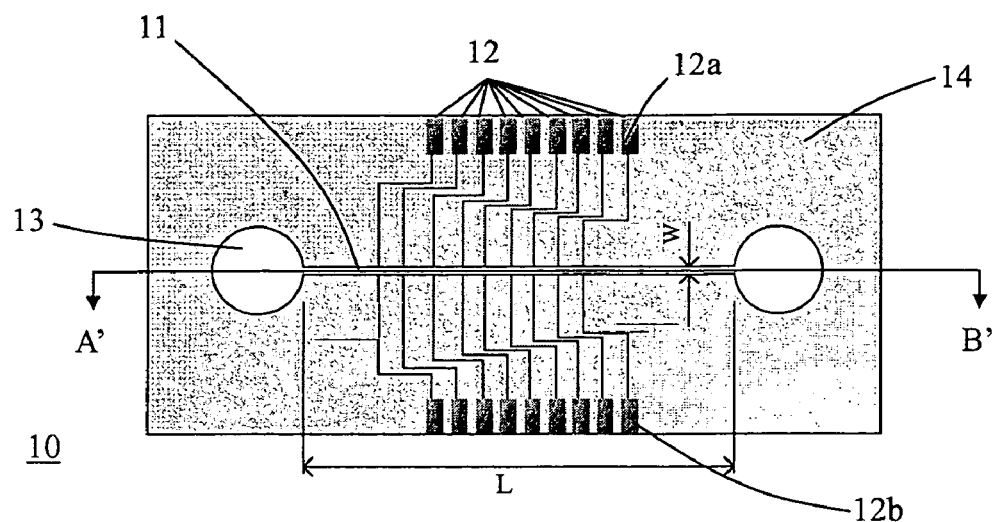
FIG. 1(a) is a top-viewing layout diagram illustrating the channels and plural pairs of electrodes for the present application.
FIG. 1(b) is a lateral-viewing layout diagram illustrating the channels and plural pairs of electrodes for the present application.
Figure 1:
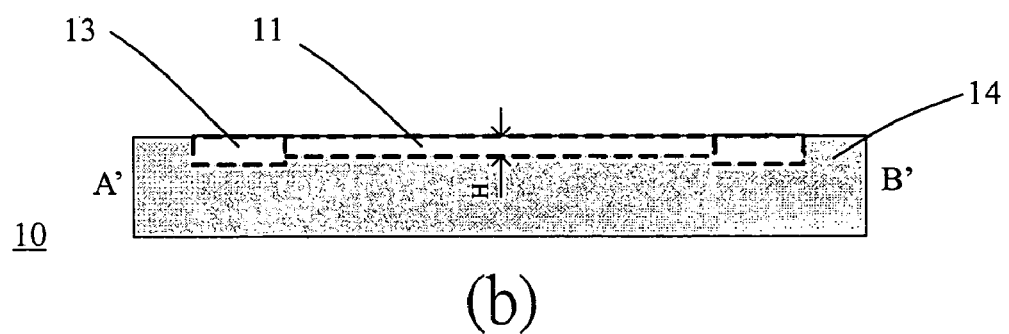

Please refer to FIG. 1(a), which is a top-viewing layout diagram illustrating the channels and plural pairs of electrodes for the present application. In the meantime, please also refer to FIG. 1(b), which is a lateral-viewing layout diagram illustrating the channels and plural pairs of electrodes for the present application. The flow measuring device 10 in FIG. 1(a) and FIG. 1(b) include a channel 11, a plural pairs of electrodes 12, a electrode 12a, a electrode 12b, a buffer zone 13 and a base 14, wherein the length of the channel 11 is L, the width of the channel 11 is W and the height of the channel is H, which the channel 11 having at least two sections is mounted on the base 14. The plural pairs of electrodes 12 are used to measure a plural variation signals corresponding to the respective at least two sections of the channel 11 flowing the fluid therein. The fluid is constituted of a gas and a liquid, with a gas-liquid interface interposed between the gas and the liquid, or of two liquids of different permittivity, with a liquid-liquid interface interposed between the two liquids.

As shown in FIG. 1(a) and FIG. 1(b), the plural pairs of electrodes 12 are constituted of at least two pairs of electrodes and are implemented from the upstream to the downstream of the channel 11. One pair of the plural pairs of electrodes 12 includes two electrodes: the electrode 12a and the electrode 12b, which are made of metal pieces. The electrode 12a and the electrode 12b are deployed in the way that they are in communication with said channel, either placed along the axial direction of said channel or symmetrically mounted at both sides of the channel, and are closely implemented but not in contact with each other (close to yet separate from each other). Since the distance between the plural pairs of electrodes 12 is known in advance, a volume containing the fluid among the plural pairs of electrodes 12 can also be determined.

The volumetric method is adopted as the working principle of the flow measuring device. The working principle thereof is introduced as follows: a liquid flows into the buffer zone 13 and then flows into the channel 11. When the liquid flows into the channel 11, a gas-liquid interface (not shown in the Figure) is formed between the liquid and the air originally existed in the channel 11, which gas-liquid interface moves toward the downstream of the channel 11 in the wake of flowing. When the liquid flows by one pair of the plural pairs of electrodes 12, the electric circuit connected to the one pair of the plural pairs of electrodes 12 turns into a closed circuit from the open circuit state, and since the resistance of water is much smaller than that of the gas, a resistance variation signal is detected by the pair of electrodes. As the gas-liquid interface moves toward the downstream of the channel 11, a resistance variation signal is generated in sequence by each of the plural pairs of electrodes 12 by which the gas-liquid interface flows. A time difference between each of the plural resistance variation signals is measured, together with the predetermined volume of the liquid contained between each pair of the plural pairs of electrodes 12, the micro flow rate of the fluid in the channel 11 can then be obtained via the ratio of the volume to the time difference.

The intention of designing plural pairs of electrodes is to adapt to different requirements for high and low flow conditions within a tolerable time duration for measurement. For example, when the flow rate is high, two pairs of electrodes far away from each other are selected to measure the flow, whereas when the flow rate is low, two pairs of electrodes located closely are adopted. Besides, multiple pairs of electrodes are helpful for obtaining plural measurements to meet the needs of individual user, and for computing the mean value so as to reduce the errors. Thus in the practical application, the user can arbitrarily pick one of the plural pairs of electrodes 12 upstream of the channel 11 as the beginning electrode, and similarly, one downstream as the terminal electrode.

The possible inaccuracies of using the flow-measuring device are sourced from the dimension effect at the sensing end of the electrode. Hence it is advised to have the signal to noise ratio (SNR) be an acceptable level, and to minimize the width of the electrodes, which otherwise would augment the transition zone of voltage rising and, as a result, affect the accuracy of the measurements.

The channel of the flow measuring device can be used in a parallel combination manner so as to accommodate the measurement capability to different flow ranges. Please refer to FIG. 2, which is a diagram illustrating the implementation of the channel in parallel connection for the flow measuring device in the present application. The flow measuring device 20 in FIG. 2 includes plural bases 21, a first channel 22a, a second channel 22b, a third channel 22c, plural pairs of electrodes 23, plural pipes 24, plural valves 25, a multiplexer 26, two sets of resistance/voltage transformer 27, and plural wires 28. Wherein when the flow measuring device is practically being operated, the resistance variation signals generated by the plural pairs of electrodes 23 corresponding to the gas-liquid interface must be transformed into measurable voltage signals. Therefore, the two sets of resistance/voltage transformer 27 are used to transform the resistance variation signals generated by two of the plural pairs of electrodes 23 into the measurable voltage signals. The plural pairs of electrodes 23, the multiplexer 26, the two sets of resistance/voltage transformer 27 and the plural wires 28 constitute at least two electric circuits. The multiplexer 26 has processors therein (not shown in the FIG. 2)

Figure 2:
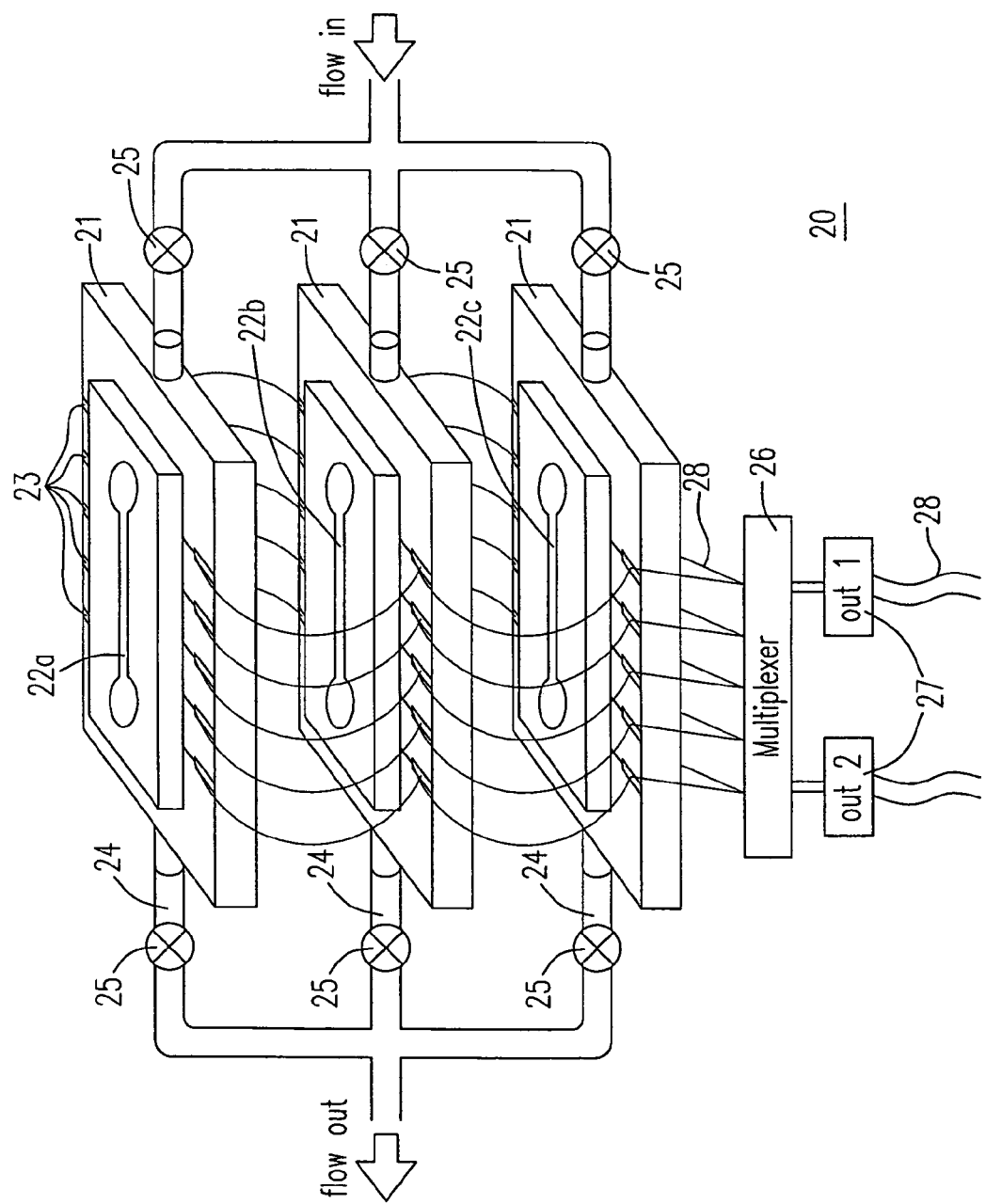
FIG. 2 is a diagram illustrating the implementation of the channel in parallel connection for the flow measuring device in the present application.

As shown in FIG. 2, the three channels 22a, 22b and 22c suitable for different flow range are in parallel connection, and each of which is suitable for a specific flow range. In order to obtain the measurement results within a reasonable time period, the default maximum and minimum tolerable measuring time duration of the device is set as 30 minutes and 0.5 minute, respectively. Based on the maximum and minimum time duration, the size and suitable flow measuring capability of the channels 22a, 22b and 22c are designed as follows:

The first channel 22a: L=35 mm, W=5 mm, H=3 mm, the maximum measurable flow $Q_{max}$=1.05 mL/min, the minimum measurable flow $Q_{min}$=0.0175 mL/min.

The second channel 22b: L=30 mm, W=2 mm, H=0.2 mm, the maximum measurable flow $Q_{max}$=0.024 mL/min, the minimum measurable flow $Q_{min}$=0.4 µL/min.

The third channel 22c: L=25 mm, W=0.6 mm, H=20 µm, the maximum measurable flow $Q_{max}$=0.6 µL/min, the minimum measurable flow $Q_{min}$=0.01 µL/min.

By combining the channels 22a, 22b and 22c in parallel connection, the measurement capability of the flow measuring device in the present invention is of the range from 1.05 mL/min to 0.01 µL/min. As an integration, the aforementioned flow measuring range of the three channels 22a, 22b and 22c can be summarized as follows:

the first channel 22a: Q=0.0175 mL/min-1.05 mL/min;

the second channel 22b: Q=0.4 µL/min-0.024 mL/min; and the third channel 22c: Q=0.01 µL/min-0.6 µL/min.

The plural pipes 24 are adopted by the channels 22a, 22b and 22c for conducting a liquid flowing thereinto. Each of the plural pipes 24 has the plural valves 25 designed to open/close independently so as to control the liquid to flow into one of the channels 22a, 22b, and 22c. The plural pairs of electrodes 23 are electrically connected with the multiplexer 26 via the plural wires 28. With the help of the multiplexer 26, the user can arbitrarily select two of the plural pairs of electrodes to be the beginning and terminal electrodes. The resistance variation signals detected by the two pairs of electrodes are each processed by one of the two sets of resistance/voltage transformer 27 and thereby obtain the time difference between the signals of the two pairs of electrodes.

Figure 3:
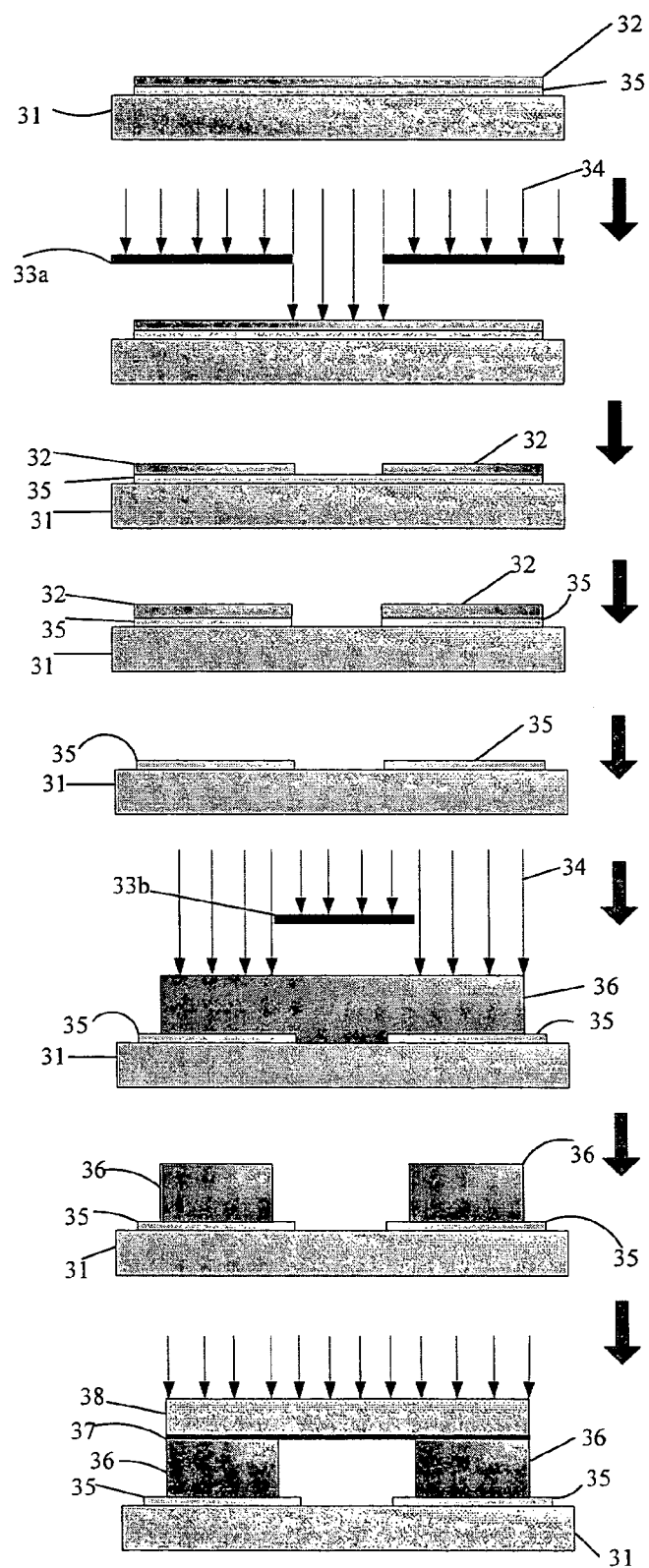
FIG. 3 is a flow chart illustrating fabrication procedures for the flow measuring device in the present application.

The foregoing flow measuring device is fabricated by a standard Micro-Electromechanical Systems (MEMS) process so as to prevent liquid leakage and channel deformation. Please refer to FIG. 3, which is a flow chart illustrating the fabrication procedures for the flow measuring device in the present application. The flow measuring device 30 in FIG. 3 includes a base 31, a positive photoresist layer 32, a photomask 33a, a photomask 33b, a UV ray 34, a metal layer 35, a thick negative photoresist 36, an adhesive 37 and a glass 38.

The fabrication steps for the flow measuring device is as follows:

(a) having the base 31 depositing the metal layer 35 thereon, which base 31 has been cleaned by a standard cleaning procedure;

(b) forming the positive photoresist layer 32 (AZ series) on the metal layer 35 by spin coating method;

(c) masking the positive photoresist layer 32 with the photomask 33a and exposing the positive photoresist layer 32 to the UV ray 34 so as to pattern the positive photoresist layer 32;

(d) removing the exposed part of the positive photoresist layer 32 by the developer, in the meantime the unexposed part of the positive photoresist layer 32 is left on the base 31, wherein the remaining photoresist reveals the configuration of the plural pairs of electrodes 12;

(e) removing the part of the metal layer 35 without the coverage of the positive photoresist layer 32 by etching;

(f) removing all the positive photoresist layer 32 by acetone or Aleg-310, and the remaining metal layer 35 on the base 31 makes the layout of the plural pairs of electrodes 12;

(g) forming the thick negative photoresist layer 36 (SU8) on the base 31 and the metal layer 35 by the spin coating method;

(h) masking the thick negative photoresist layer 36 with the photomask 33b and exposing the thick negative photoresist layer 36 to the UV ray 34 so as to pattern the thick negative photoresist layer 36;

(i) removing the unexposed part of the thick negative photoresist layer 36 by the developer, in the meantime the exposed part of the thick negative photoresist layer 36 is left on the base 31, wherein the remaining photoresist forms the channel 11;

(j) applying a thin negative photoresist layer (SU8) as the adhesive 37 to the glass 38; and (k) assembling the glass 38 to the base 31 and exposing all to the UV ray 34 so as to render the thick negative photoresist 36 and the adhesive 37 bonded tightly. The fabrication of the flow measuring device is accomplished.

The foregoing steps are a standard Micro-Electromechanical Systems (MEMS) produce. Wherein a thin metal layer 35 in the step (a) is formed on the base 31 by a sputtering deposition method or E-beam evaporation deposition method. Furthermore, the spin coating method in step (b) is performed as follows: placing the base 31 on a turntable and drawing the base 31 onto the turntable by vacuuming, injecting the positive photoresist layer 32 from the center of the base 31 by an injector, having the positive photoresist layer 32 spread over the base 31, rotating the turntable, and, as a result, having the positive photoresist layer 32 applied on the base 31 in uniformity. A similar procedure holds for steps (g) and (j) in forming the negative photoresist layers.

The photomasks 33a and 33b in step (c) and (h) are the masks for preventing the photoresist from UV ray exposure which is associated with the subsequent developing steps (d) and (i). In general, the photomask is fabricated in advance by etching method or have it made by photomask companies. Wherein the photomask 33a is a positive photomask whose patterning picture is the plural pairs of electrodes 12, and the photomask 33b is a negative photomask whose pattering picture is the channel 11. The aforementioned steps (d) and (i) are the developing processes, which take advantage of the property that the character of photoresist is changed after exposed to the ultraviolet ray. Generally, photoresists are categorized into positive photoresist and negative photoresist. If the photoresist exposed to the ultraviolet ray becomes dissolvable to the developer, such photoresist is termed as positive photoresist. The unexposed part of the positive photoresist will remain after the developing procedure and form a thin acid-proof layer serving as a blocking shell during the subsequent processes such as etching, and the exposed part is dissolved while developing. On the other hand, if the photoresist exposed to the ultraviolet ray turned indissoluble to the developer, such photoresist is termed as negative photoresist. The exposed part of the negative photoresist will remain after the developing procedure and form a thin acid-proof layer serving as a blocking shell during the subsequent processes such as etching, and the unexposed part is dissolved while developing.

Ordinarily, the positive photoresist bears fine resolution and explicit contrast so as to obtain more slender line width, and hence is extensively used by the industrial field. However, it is suggested to process the positive photoresist under the circumstances that the relative humidity is within the range from 45% to 50% for obtaining a good adhesion, otherwise it is easy to flake off. In contrast to the positive photoresist, the negative photoresist is rather robust, and can still be used under circumstances with higher humidity level. Therefore, both the positive and negative photoresist are adopted in the present application and are used when whichever is deemed more suitable.

Figure 4:
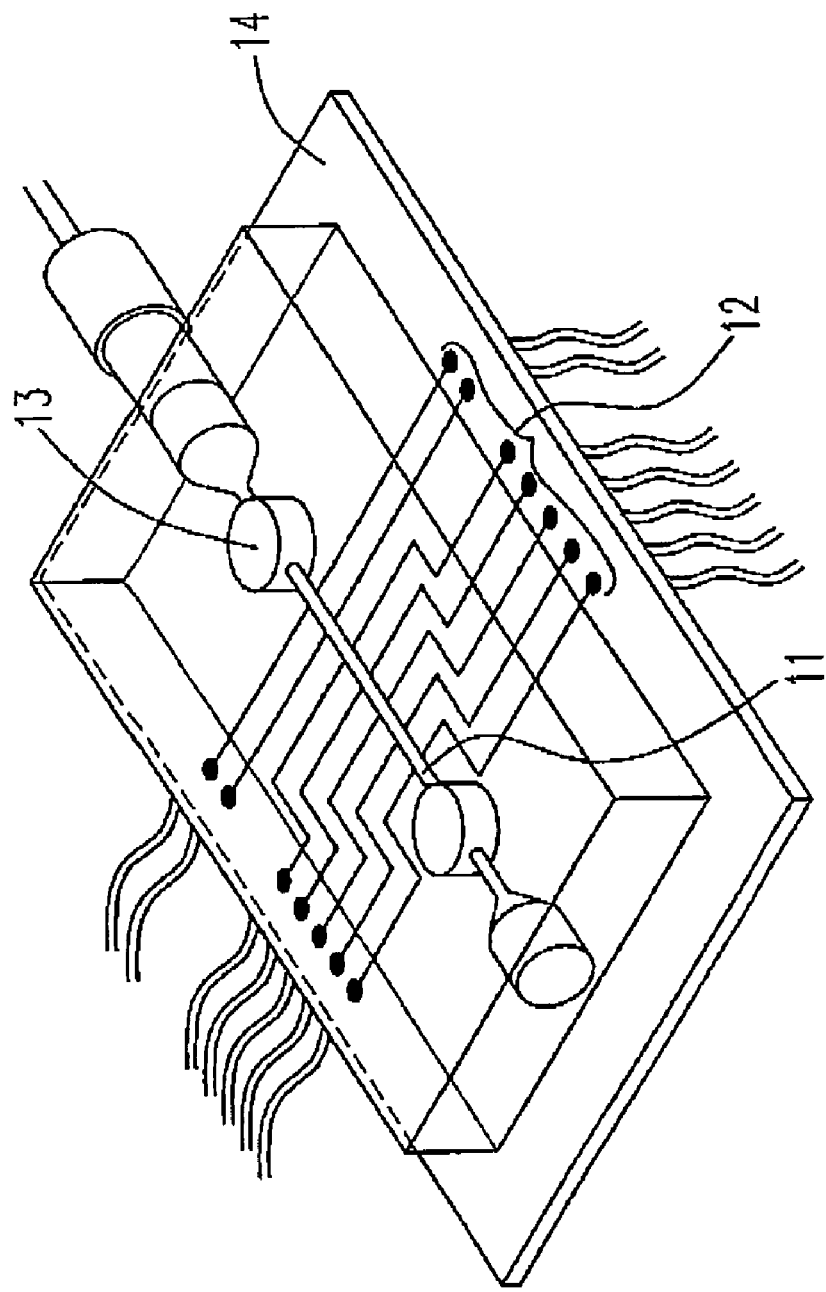
FIG. 4 is the schematic diagram of the flow measuring device fabricated by the aforementioned MEMS system in the present application.

Please refer to FIG. 4, which is the schematic diagram of the flow measuring device fabricated by the aforementioned MEMS system in the present application. When the flow measuring device is practically put to use, a function generator is first adopted to input a 2-3 kHz, 5 V sinusoidal signal to the plural pairs of electrodes with which a high impedance resistance (2.4MΩ) is serially connected. In addition, an adjustable amplifying electric circuit is connected in parallel with the measuring electrodes so as to regulate the voltage signal before it is outputted. When the channel is filled with gas, in other words, empty, the electric circuit is in the open circuit status, and the waves shown on the oscilloscope is merely the signals generated by the signal sources. However, at the moment when the liquid flows into the channel and passes by the measuring electrodes, the resistance existing in the electric circuit is decreased dramatically. Consequently, a resistance variation yields a voltage variation upon the transformation provided by the resistance/voltage transformers, resulting in a voltage drop in the electric circuit consisted of the pair of the electrodes by which the liquid flowed. A resistance variation signal is generated in sequence by each of the plural pairs of electrodes 12 by which the gas-liquid interface passes. Thus the time period between two voltage jumps (or drops, depending on the flow direction) corresponding to two different pairs of electrodes is used to calculate the flow in the subsequent steps.

Figure 5:
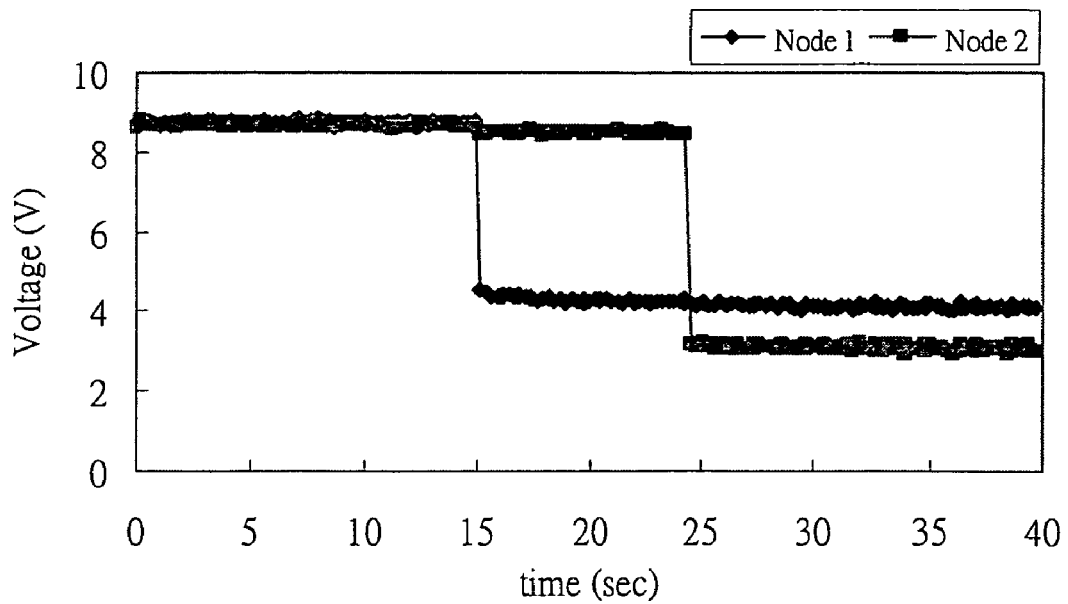
FIG. 5 is a relative relation diagram of the resistance variation signal between two pairs of electrodes in the present application.

Please refer to FIG. 5, which is a diagram of the voltage variation versus time of two pairs of electrodes in the present application. The two curves shown in FIG. 5 correspond to the voltage variation of two arbitrarily selected pairs of electrodes, one beginning and one terminal. Here, a threshold can be set, for example, 10% of the voltage deviation between the maximum and minimum values, as the reference trigger for extracting the time period ($\Delta t$) between the two voltage jumps from the voltage variation curves. Furthermore, the volume between two pairs of electrodes ($\Delta V$) is known in advance, thus the flow rate (Q) can be computed by having the volume ($\Delta V$) divided by the time period ($\Delta t$), namely, $Q=\Delta V/\Delta t$. Please be noted that although the present preferred embodiment is focused on water, it is to be understood that the invention needs not to be limited to the disclosed embodiment. For example, the flow measuring device of the present invention is also suitable for measuring the flow of electric conductive liquid.

In summary, the concept of the present application is to estimate a flow rate in the channel by the ratio of a known volume to the measured time period. The measuring method herein is to sense the instantaneous resistance variation associated with a fluid that passes by the two sensing electrodes which are close to yet separate from each other. When two pairs of electrodes, one upstream and one downstream of the channel, are targeted, since the volume in between is predetermined (with known channel characteristics and distance between electrode pairs), and the time period for the liquid to flow through can be determined from the corresponding resistance variation signals, the flow can then be obtained thereupon.

In contrast to the ordinary thermal type or pressure gradient type flow meters, the advantage of the present invention is to practically measure physical parameters rather then the results transformed by the formulations. Therefore, after calibration, the present invention would be able to serve as a working standard, or to connect in series with other types of flow meters to perform a direct comparison.

In other words, the proposed method is characterized in that the measurement for the flow is performed by tracing either of a gas-liquid interface or a liquid-liquid interface. Usually, when two fluids having different permittivity and undissolvable to each other come in contact with each other, a gas-liquid interface or a liquid-liquid interface is exactly formed at the contact front, for the condition that two fluids are composed of gas and liquid or liquid and liquid, respectively. For example, a gas-liquid interface is exactly formed at the contact front where air and water come in contact with each other, and a liquid-liquid interface is exactly formed at the contact front where oil and water come in contact with each other. Therefore, from another point of view, the present invention measures the flow by tracing the interface between multiple fluids.

In conclusion, as compared with the conventional miniature flow meters, the flow measuring device detects the flow volume and the time period using plural pairs of electrodes without any transformation upon the formulations. Thus the flow measuring device is potentially more accurate than other miniature flow meters such as the thermal type and the pressure gradient type. In particular, by combing the channels of different measurable flow range in parallel connection, the verifiable range of the flow measuring device set can be increased/decreased according to the needs of individual user; it is thus capable of meeting the diverse requirements in the future.

While the invention has been described in terms of what are presently considered to be the most practical and preferred embodiments, it is to be understood that the invention need not to be limited to the disclosed embodiment. On the contrary, it is intended to cover various modifications and similar arrangements included within the spirit and scope of the appended claims that are to be accorded with the broadest interpretation, so as to encompass all such modifications and similar structures. Accordingly, the invention is not limited by the disclosure, but instead its scope is to be determined entirely by reference to the following claims.

What is claimed is:

1. A device for measuring a flow of a fluid, comprising:
   a base;
   a channel mounted on said base flowing said fluid therein and having at least two sections; and
   at least two electronic circuits electrically connected to said respective at least two sections and detecting a respective variation signal corresponding to said respective at least two sections so as to obtain said flow according to said respective variation signal, wherein each of said at least two electronic circuits includes at least a pair of electrodes disconnected from each other.

2. The device according to claim 1, wherein said pair of electrodes are mounted on said base in communication with said channel.

3. The device according to claim 1, wherein said pair of electrodes are a pair of metal pieces along the axial direction of said channel or symmetrically mounted at two sides of said channel, close to yet separate from each other.

4. The device according to claim 1 wherein said respective variation signal is a resistance variation corresponding to said respective at least two sections and are detected by said respective at least two electronic circuits.

5. The device according to claim 1, wherein said fluid has a gas-liquid interface or a liquid-liquid interface, while said gas-liquid interface or said liquid-liquid interface passing each of said sections, said respective variation signal at said respective at least two electronic circuits is determined by said gas-liquid interface or said liquid-liquid interface.

6. The device according to claim 5, wherein the gas-liquid interface is an air-water interface.

7. The device according to claim 5, wherein the liquid-liquid interface is an oil-water interface.

8. The device according to claim 1 wherein:
   when said fluid in said channel is a liquid and when said liquid flows by one pair of electrodes, an electric circuit connected to said one pair of electrodes turns into a closed circuit from an open circuit state.

9. The device according to claim 1 wherein;
each pair of electrodes disconnected from each other are located symmetrically on two sides of said channel.

10. The device according to claim 1 wherein:
a signal is detected by one pair of electrodes when a liquid in said channel flows by said one pair of electrodes.

11. A device for measuring a flow of a fluid, comprising:
a plurality of bases;
a plurality of channels, mounted on said respective plurality of bases and flowing said fluid therein, wherein each of said plurality of channels has at least two sections; and
at least two electronic circuits electrically connected to said respective at least two sections and detecting a respective variation signal corresponding to said respective at least two sections so as to obtain said flow according to said respective variation signal, wherein each of said at least two electronic circuits includes at least a pair of electrodes disconnected from each other.

12. The device according to claim 11, wherein said pair of electrodes are mounted on said base in communication with said channel.

13. The device according to claim 11, wherein said pair of electrodes are a pair of metal pieces placed along the axial direction of said channel or symmetrically mounted at two sides of said channel, close to yet separate from each other.

14. The device according to claim 11 wherein said respective variation signal is a resistance variation corresponding to said respective at least two sections and is detected by said respective at least two electronic circuits.

15. The device according to claim 11, wherein said fluid has a gas-liquid interface or a liquid-liquid interface, while said gas-liquid interface or said liquid-liquid interface passing each of said sections, said respective variation signal at said respective at least two electronic circuits is determined by said gas-liquid interface or said liquid-liquid interface.

16. The device according to claim 15, wherein the gas-liquid interface is an air-water interface.

17. The device according to claim 15, wherein the liquid-liquid interface is an oil-water interface.

18. The device according to claim 11, wherein said plurality of channels is mutually parallel for measuring different flow rates of said fluid.

19. The device according to claim 11, wherein said flow rate is in a range from 1.05 mL/min to 0.01 μL/min.

20. A device for measuring a micro fluid, comprising:
a processor; and
at least two electronic circuits electrically connected to said processor and respectively detecting a variation signal so as to obtain a flow rate of said micro fluid according to said variation signal, wherein each of said at least two electronic circuits includes at least a pair of electrodes disconnected from each other.

21. The device according to claim 20, wherein said pair of electrodes include at least a pair of metal pieces.

22. The device according to claim 20 wherein said variation signal is a resistance variation at a respective location of said micro fluid and is detected by said respective at least two electronic circuits.

23. The device according to claim 20, wherein said micro fluid has a gas-liquid or a liquid-liquid interface.

24. The device according to claim 23, while said gas-liquid or liquid-liquid interface passing each of said two locations, said respective variation signal at said respective at least two electronic circuits is determined by said gas-liquid or liquid-liquid interface.

25. The device according to claim 23, wherein the gas-liquid interface is an air-water interface.

26. The device according to claim 23, wherein the liquid-liquid interface is an oil-water interface.

* * * * *